(12) United States Patent
Vedso et al.

(10) Patent No.: US 6,872,849 B2
(45) Date of Patent: Mar. 29, 2005

(54) HALO SULFONYL ARYL BORONATES

(75) Inventors: Per Vedso, Vaerlose (DK); Preben Houlberg Olesen, Copenhagen (DK); Thomas Hoeg-Jensen, Klampenborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/697,226

(22) Filed: Oct. 30, 2003

(65) Prior Publication Data

US 2004/0116701 A1 Jun. 17, 2004

Related U.S. Application Data

(60) Provisional application No. 60/425,579, filed on Nov. 12, 2002.

(30) Foreign Application Priority Data

Nov. 8, 2002 (DK) .......................... 2002 01723

(51) Int. Cl.⁷ ..................... C07F 5/02; C07C 309/00
(52) U.S. Cl. .................... 562/7; 562/828; 562/832; 562/833
(58) Field of Search .................... 562/7, 828, 832

(56) References Cited

FOREIGN PATENT DOCUMENTS

WO    WO 02/32884 A2   4/2002

OTHER PUBLICATIONS

Dicesare et al., STN Database accession No. 768624 Zcaplus [online], Abstract & Chemical Communications, vol. 19, pp. 2022–2023 (2001).

International Search Report mailed Mar. 19, 2004.

Bielecki et al., J. Chem. Soc., Perkin Trans. 2, pp. 449–455 (1999).

Eggert et al., J. Org. Chem., vol. 64, pp. 3846–3852 (1999).

Shinkai et al., Trends in Analytical Chemistry, vol. 15, No. 5, pp. 188–194 (1996).

*Primary Examiner*—Paul A. Zucker
(74) *Attorney, Agent, or Firm*—Reza Green, Esq.; Richard W. Bork, Esq.; Rosemarie R. Wilk-Drescan, Esq.

(57) ABSTRACT

The present invention relates to halo sulfonyl aryl boronates of the general formula (I):

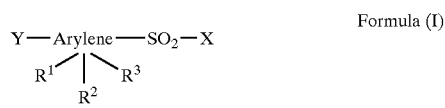

Formula (I)

wherein Arylene designates a carbocyclic or heterocyclic, aromatic ring system comprising 1–3 rings;

$R^1$, $R^2$ and $R^3$ are, independently, hydrogen, $C_{1-6}$alkyl, $C_{1-6}$alkoxy, halogen, nitro, cyano or phenyl;

X is fluoro, chloro or bromo; and

Y is a boroxine moiety attached via a bond from Arylene to one of the boron atoms of a boroxine ring which ring has a group of the formula -Arylene($R^1$)($R^2$)($R^3$)$SO_2$X, wherein Arylene, $R^1$, $R^2$, $R^3$ and X are as defined above, at each of the other two boron atoms of the boroxine ring, or Y is a boronic acid group or a boronic ester group. The invention also relates to the preparation of the compounds of formula (I) and to their use in organic synthesis.

13 Claims, No Drawings

HALO SULFONYL ARYL BORONATES

CROSS-REFERENCE TO RELATED APPLICATIONS

This application claims priority under 35 U.S.C. 119 of Danish application no. PA 2002 01723 filed Nov. 8, 2002 and U.S. application Ser. No. 60/425,579 filed Nov. 12, 2002, the contents of each of which are fully incorporated herein by reference.

FIELD OF THE INVENTION

The present invention relates to halo sulfonyl aryl boronates, to their preparation and to their use in organic synthesis.

BACKGROUND OF THE INVENTION

Boronates, the anionic counterpart of boronic acids, are known to bind carbohydrates via reversible ester formation, with apparent displacement constants ($K_d$'s) of approximately 0.1–20 mM, which make them suitable for measuring glucose and other carbohydrates in the physiologically relevant range (Shinkai and Takeuchi, Trends Anal. Chem. 1996, 15, 188). However, since simple phenylboronic acid displays a pKa value of approximately 8.5, the formation of phenylboronates of carbohydrates is unfavoured under physiological conditions (pH 7.4). Accordingly, the binding of carbohydrates to phenylboronic acid is weak under physiological conditions. A stronger binding of carbohydrates at pH values around 7.4 can be achieved with boronic acids having a lower pKa, for example with phenyl boronic acids having electron-withdrawing groups in the aromatic ring (Eggert et al., J. Org. Chem. 1999, 64, 3846), or by introducing a 2-aminomethyl substituent, which locks boron in a tetrahedral state via B—N interaction (Bielecki, Eggert and Norrild, J. Chem. Soc., Perkin Trans 2 1999, 449).

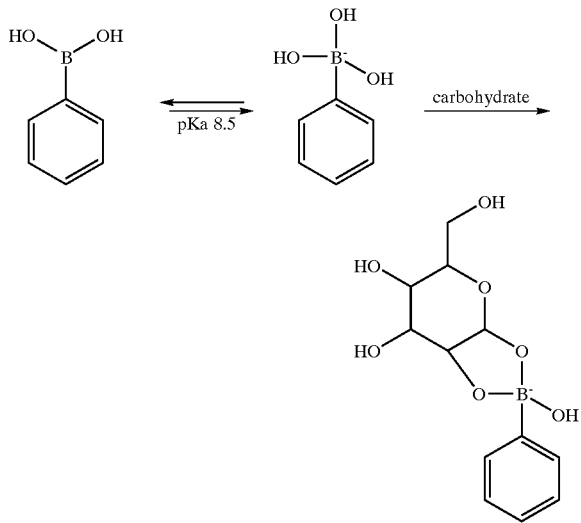

The sulfonyl functional group is strongly electron-withdrawing, and it can furthermore function as a handle, because e.g. sulfonate halides can be coupled to other molecules. However, although sulfonyl halides of aryl boronic acids would be useful intermediates in organic synthesis such compounds and methods for their preparation have not been described in literature.

SUMMARY OF THE INVENTION

In one aspect, the present invention relates to sulfonyl halides of the general formula (I)

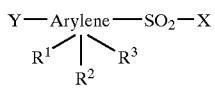

Formula (I)

wherein Arylene designates a carbocyclic or heterocyclic, aromatic ring system comprising 1–3 rings;

$R^1$, $R^2$ and $R^3$ are, independently, hydrogen, $C_{1-6}$alkyl, $C_{1-6}$alkoxy, halogen, nitro, cyano or phenyl;

X is fluoro, chloro or bromo; and

Y is a boroxine ring, or Y is a boronic acid group or an alkyl boronate group.

In one embodiment of the invention, Arylene designates a carbocyclic, monocyclic ring system, for example a benzene ring, to which $R^1$, $R^2$, $R^3$, $SO_2$—X and Y are covalently bound.

In another embodiment, Arylene designates a carbocyclic, bicyclic ring system, for example naphthalene, to which $R^1$, $R^2$, $R^3$, $SO_2$—X and Y are covalently bound.

In a further embodiment, Arylene designates a carbocyclic, tricyclic ring system, for example antracene, to which $R^1$, $R^2$, $R^3$, $SO_2$—X and Y are covalently bound.

In a further embodiment, Arylene designates a heterocyclic, monocyclic ring system, for example pyridine or thiophene, to which $R^1$, $R^2$, $R^3$, $SO_2$—X and Y are covalently bound.

In further embodiment, Arylene designates a heterocyclic, bicyclic ring system, for example quinoline, to which $R^1$, $R^2$, $R^3$, $SO_2$—X and Y are covalently bound.

In further embodiment, Arylene designates a heterocyclic, tricyclic ring system, to which $R^1$, $R^2$, $R^3$, $SO_2$—X and Y are covalently bound.

In a further embodiment of the invention, $R^1$, $R^2$ and $R^3$ are all hydrogen.

In a further embodiment, two of $R^1$, $R^2$ and $R^3$ are hydrogen while the third substituent is selected from the group consisting of $C_{1-6}$alkyl, $C_{1-6}$alkoxy, halogen, nitro, cyano and phenyl. In one particular form of this embodiment, the non-hydrogen substituent is fluoro, in another particular form it is chloro and in a third particular form it is bromo.

In a further embodiment, one of $R^1$, $R^2$ and $R^3$ are hydrogen while the other two substituents are selected, independently, from the group consisting of $C_{1-6}$alkyl, $C_{1-6}$alkoxy, halogen, nitro, cyano and phenyl. In particular forms of this embodiment, the non-hydrogen substituents can, independently, be fluoro, chloro or bromo.

In a further embodiment of the invention, X is flouro.

In a further embodiment, X is chloro.

In a further embodiment, X is bromo.

In a further embodiment of the invention, Y is a boroxine moiety attached via a bond from Arylene to one of the boron atoms of a boroxine ring which ring has a group of the formula -Arylene($R^1$)($R^2$)($R^3$)$SO_2X$, wherein Arylene, $R^1$, $R^2$, $R^3$ and X are as defined above, at each of the other two boron atoms of the boroxine ring as well.

In a further embodiment, Y is a boronic acid group, that is, a group of the formula —B(OH)$_2$.

In a further embodiment, Y is a boronic acid ester group. In a particular form of this embodiment, the boronic acid ester is an ester derived from boronic acid and a diol.

One particular example of this form is shown in formula (a) below.

Another particular example of this form is shown in formula (b) below in which R is methyl, ethyl, propyl, isopropyl, butyl, isobutyl, tert-butyl or phenyl.

Another particular example of this form is shown in formula (c) below in which R is methyl, ethyl, propyl, isopropyl, butyl, isobutyl, tert-butyl or phenyl.

Another particular example of this form is shown in formula (d) below in which R is methyl, ethyl, propyl, isopropyl, butyl, isobutyl, tert-butyl or phenyl.

Another particular example of this form is shown in formula (e) below.

Another particular example of this form is shown in formula (f) below.

Another particular example of this form is shown in formula (g) below.

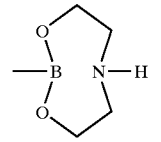

(a)

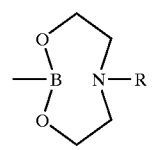

(b)

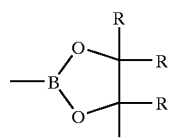

(c)

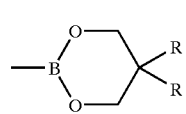

(d)

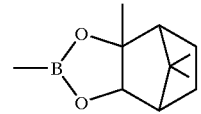

(e)

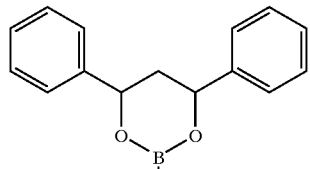

(f)

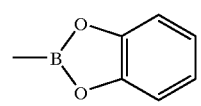

(g)

In another aspect, the present invention relates to a method for the preparation of the compounds of formula (I) as defined above. The method of preparation comprises the following steps:

a) reacting a compound of formula (II):

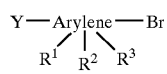

Formula (II)

wherein $R^1$, $R^2$, $R^3$ and Y are as defined above, in an inert solvent at a temperature below −75° C. with butyl lithium to form a lithiated intermediate of formula (III):

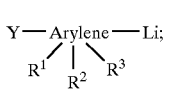

Formula (III)

b) adding sulfur dioxide to the lithiated intermediate of formula (III) to form the corresponding lithium sulfinate of formula (IV):

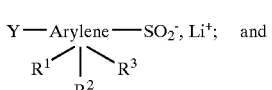

Formula (IV)

c) converting the lithium sulfinate of formula (IV) to the corresponding sulfonylchloride of formula (I) by treating the lithium sulfinate with an oxidizing chlorinating agent such as N-chlorosuccinimide (NCS) or 1,3-dichloro-5,5-dimethylhydantoin or to the corresponding sulfonylbromide by treating the lithium sulfinate with an oxidizing brominating agent such as N-bromosuccinimide.

As an alternative to step b) and c), the lithiated intermediate of formula (III) can be sulfonylated with sulfur trioxide and then fluorinated with sulfur tetrafluoride or diethylamino sulfur trifluoride to produce the corresponding sulfonylfluoride of formula (I), or the lithiated intermediate of formula (III) can be sulfonylated with sulfur trioxide and chlorinated with thionyl chloride, sulfuryl chloride, phosphortrichloride, phosphorpentachloride or phosphoroxychloride to produce the corresponding sulfonylchloride of formula (I).

In a further aspect, the present invention relates to the use of the compounds of formula (I) as building blocks in organic chemistry. Thus, on reaction with ammonia, with primary amines or with secondary amines the compounds of formula (I) will form the corresponding amides.

DETAILED DESCRIPTION OF THE INVENTION

In the preparation of the compounds of the invention, halo aryl boronic acids, preferable in the form of their N-methyl-diethanolamine esters, are dissolved in an inert solvent and cooled to low temperature, preferably −90 to −105° C. Examples of suitable solvents for the reaction are tetrahydrofuran, diethylether, dioxane in mixture with a solvent having a low freezing point, diglyme, tert-butylmethylether, di-tert-butylether, tetrahydropyran, and mixtures thereof. When choosing the solvent or solvent mixture, the freezing point of the solvent or solvent mixture must be taken into consideration so that it does not freeze at the temperature at which the reaction is carried out.

While a temperature between −90° C. and −105° C. may be convenient in many cases it is of course possible to work at higher temperatures, for example −75° C. or even −60° C. and lower temperatures, for example −120° C. or −150° C.

After butyl lithium in hexane has been added to the solution of the starting material, the resulting lithiated aryl is quenched by addition of sulfur dioxide to form the corresponding sulfinate or sulfur trioxide to form the corresponding sulfonate. The lithium sulfinate precipitates and is collected by filtration. The sulfinate is oxidized and halogenated, preferably in a simultaneous process by treatment with an N-chloro compound, such as 1,3-dichloro-5, 5-dimethylhydantoin, or by treatment with N-bromosuccinimide to form the sulfonylbromide of formula (I). Alternative halogenating agents are thionyl chloride, sulfuryl chloride, phosphortrichloride, phosphorpentachloride, phosphoroxychloride, sulfur tetrafluoride and diethylamino sulfur trifluoride which can be used to halogenate the lithium sulfonates.

The halo sulfonyl phenyl boronates can be isolated by aqueous work-up, or used in situ for coupling to amines or other nucleophiles.

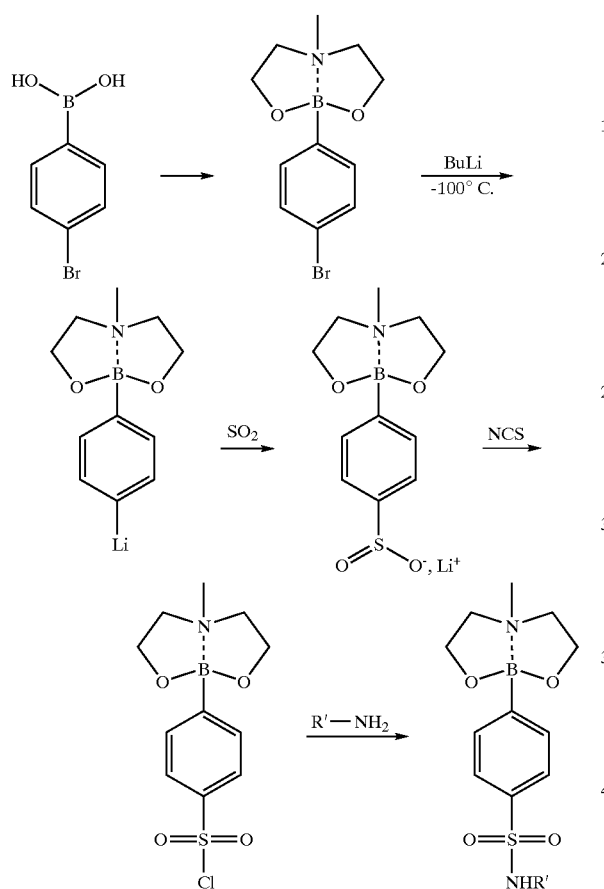

Sulfonylamide aryl boronates prepared by the described route are emendable to cross-coupling reactions (A. Suzuki, Journal of Organometallic Chemistry 1999, 576, 147) as exemplified by Suzuki coupling with formation of a biphenyl compound.

EXAMPLES

Acronyms used for chemicals, groups and commercially available chemicals:

| | |
|---|---|
| DCl | Deuterium chloride |
| CDCl$_3$ | Deuterochloroform |
| DMSO | Dimethylsulfoxide |

General Methods and Materials

All reactions involving air-sensitive reagents were performed under nitrogen using syringe-septum cap techniques. The glassware was flame dried prior to use. MgSO$_4$ was used to dry solutions. Solvents were removed in vacuo by rotatory evaporation. Melting points were recorded on a Büchi 535 melting point apparatus and are uncorrected. NMR spectra were recorded on a Bruker AMX 400 or a Bruker DRX 300 instrument with tetramethylsilane (TMS) as internal standard. All solvents and reagents were obtained from commercial sources and used without further purification. Butyl lithium was titrated prior to use.

Example 1

Lithium 4-sulfinyl-phenylboronic acid N-methyl-diethanolamine ester

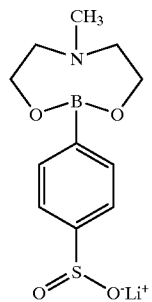

To a stirred solution of 4-bromobenzeneboronic acid N-methyldiethanolamine ester (6.62 g, 23.4 mmol) in dry tetrahydrofuran (200 mL) was added drop-wise 1.43 M solution in hexanes of n-BuLi (14.8 mL, 21.0 mmol) over a 5-min period at −105° C., using an ether-liquid nitrogen bath. The mixture was stirred at −105° C. for 15 min. Then, gaseous sulfur dioxide (ca. 7 g) was added causing an immediate precipitation and a roughly 40° C. increase in the temperature of the reaction mixture. The mixture was allowed to warm to room temperature and stirred for 1 h. The precipitated lithium sulfinate was isolated by filtration under N$_2$ (g), washed with tetrahydrofuran (100 mL) and dried in vacuo providing 5.74 g (99%) of the title compound as a solid: mp>230° C.; $^1$H NMR (DMSO-d$_6$): δ7.43 (d, 2H), 7.35 (d, 2H), 3.97–3.83 (m, 4H), 3.26–3.19 (m, 2H), 2.98–2.89 (m, 2H), 2.17 (s, 3H).

Example 2

Lithium 3-sulfinyl-phenylboronic acid N-methyl-diethanolamine ester

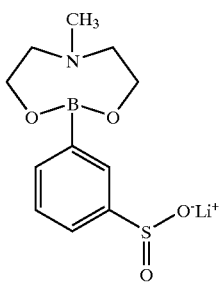

To a stirred solution of 3-bromobenzeneboronic acid N-methyldiethanolamine ester (3.31 g, 11.7 mmol) in dry tetrahydrofuran (100 mL) was added drop-wise 1.43 M solution in hexanes of n-BuLi (7.4 mL, 10.5 mmol) over a 3-min period at −78° C. The mixture was stirred at −78° C. for 15 min. Then, gaseous sulfur dioxide (ca. 5 g) was added causing an immediate precipitation and a roughly 40° C.

increase in the temperature of the reaction mixture. The mixture was allowed to warm to room temperature and stirred for 1 h. The precipitated lithium sulfinate was isolated by filtration under $N_2$ (g), washed with tetrahydrofuran (50 mL) and dried in vacuo providing 2.81 g (97%) of the title compound as a solid: $^1$H NMR (DMSO-$d_6$): δ7.66 (s, 1H), 7.39–7.32 (m, 2H), 7.17 (t, 1H), 3.97–3.84 (m, 4H), 3.27–3.21 (m, 2H), 2.97–2.89 (m, 2H), 2.18 (s, 3H).

Example 3

4-Chlorosulfonyl-phenylboronic acid N-methyl-diethanolamine ester

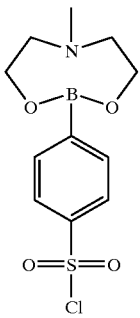

Lithium 4-sulfinyl-phenylboronic acid N-methyl-diethanolamine ester (138 mg, 0.5 mmol) was suspended in $CH_2Cl_2$ (1 mL). N-Chlorosuccinimide (73 mg, 0.55 mmol) was added and the mixture was stirred at room temperature for 1 h. The organic solution was washed three times with ice cold water and then dried and evaporated to give 80 mg (52%) of the title compound as coulorless crystals: $^1$H NMR ($CDCl_3$): δ7.94 (d, 2H), 7.89 (d, 2H), 4.29–4.14 (m, 4H), 3.28 (ddd, 2H), 3.06 (ddd, 2H), 2.36 (s, 3H).

Example 4

Lithium 4-sulfinyl-2-fluorophenylboronic acid N-methyl-diethanolamine ester

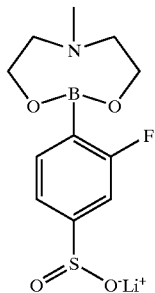

To a stirred solution of 4-bromo-2-fluorobenzeneboronic acid N-methyldiethanolamine ester (2.64 g, 8.74 mmol) in dry tetrahydrofuran (80 mL) was added drop-wise 1.6 M solution in hexanes of n-BuLi (4.91 mL, 7.85 mmol) over a 2-min period at −78° C. The mixture was stirred at −78° C. for 15 min. Then, gaseous sulfur dioxide (ca. 3 g) was added causing an immediate precipitation and a roughly 40° C. increase in the temperature of the reaction mixture. The mixture was allowed to warm to room temperature and was stirred for 1 h. The precipitated lithium sulfinate was isolated by filtration under $N_2$ (g), washed with tetrahydrofuran (50 mL) and dried in vacuo providing 2.19 g (95%) of the title compound as a solid: $^1$H NMR (DMSO-$d_6$): δ7.50 (t, 1H), 7.14 (d, 1H), 7.02 (d, 1H), 3.93–3.81 (m, 4H), 3.28–3.22 (m, 2H), 3.04–2.97 (m, 2H), 2.39 (s, 3H).

Example 5

4-Phenethylsulfamoylbenzeneboronic acid

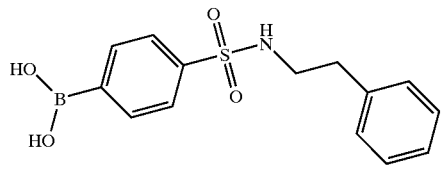

Lithium 4-sulfinyl-phenylboronic acid N-methyl-diethanolamine ester (275 mg, 1.0 mmol) was suspended in $CH_2Cl_2$ (2 mL). N-Chlorosuccinimide (147 mg, 1.10 mmol) was added and the mixture was stirred at room temperature for 1 h. 2-Phenylethylamine (0.265 mL, 2.1 mmol) was added and the reaction mixture was stirred for 1 h at room temperature. Then, Dowex 50WX2-400 cation exchange resin (about 1 g) was added and the mixture was stirred for further 1 h. The resin was removed by filtration and extracted with $CH_2Cl_2$:MeOH (9:1). To the combined organic filtrates was added 1N NaOH and the aqueous phase was washed with $CH_2Cl_2$. The aqueous phase was acidified with 1N HCl and the resulting crystals were isolated by filtration to give 154 mg (50%) of the title compound: $^1$H NMR (DMSO-$d_6$+DCl): δ7.95 (d, 2H), 7.75 (d, 2H), 7.29–7.13 (m, 5H), 2.94 (t, 2H), 2.67 (t, 2H).

Example 6

4-Benzylsulfamoylbenzeneboronic acid

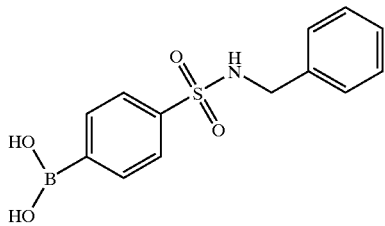

Lithium 4-sulfinyl-phenylboronic acid N-methyl-diethanolamine ester (275 mg, 1.0 mmol) was suspended in $CH_2Cl_2$ (2 mL). N-Chlorosuccinimide (147 mg, 1.10 mmol) was added and the mixture was stirred at room temperature for 1 h. Benzylamine (0.23 mL, 2.1 mmol) was added and the reaction mixture was stirred for 1 h at room temperature. Then, Dowex 50WX2-400 cation exchange resin (about 1 g) was added and the mixture was stirred for further 1 h. The resin was removed by filtration and extracted with $CH_2Cl_2$:MeOH (9:1). To the combined organic filtrates was added 1N NaOH and the aqueous phase was washed with $CH_2Cl_2$. The aqueous phase was acidified with 1N HCl and the resulting crystals were isolated by filtration to give 163 mg (56%) of the title compound: $^1$H NMR (DMSO-$d_6$+DCl): δ7.95 (d, 2H), 7.78 (d, 2H), 7.32–7.19 (m, 5H), 3.97 (s, 2H).

Example 7

4-(Methylphenethylsulfamoyl)benzeneboronic acid

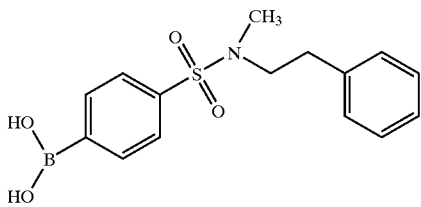

Lithium 4-sulfinyl-phenylboronic acid N-methyl-diethanolamine ester (275 mg, 1.0 mmol) was suspended in $CH_2Cl_2$ (2 mL). N-Chlorosuccinimide (147 mg, 1.10 mmol) was added and the mixture was stirred at room temperature for 1 h. Methylphenylethylamine (0.305 mL, 2.1 mmol) was added and the reaction mixture was stirred for 1 h at room temperature. Then, Dowex 50WX2-400 cation exchange resin (about 1 g) was added and the mixture was stirred for further 1 h. The resin was removed by filtration and extracted with $CH_2Cl_2$:MeOH (9:1). To the combined organic filtrates was added 1N NaOH and the aqueous phase was washed with $CH_2Cl_2$. The aqueous phase was acidfied with 1N HCl and the resulting crystals were isolated by filtration to give 196 mg (61%) of the title compound: $^1$H NMR (DMSO-$d_6$+DCl): δ7.99 (d, 2H), 7.71 (d, 2H), 7.32–7.19 (m, 5H), 3.19 (t, 2H), 2.77 (t, 2H), 2.69 (s, 3H).

Example 8

3-Benzylsulfamoylbenzeneboronic acid

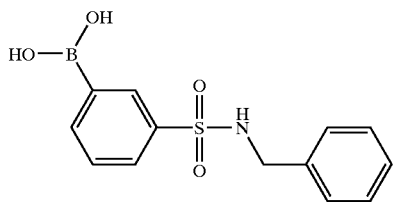

Lithium 3-sulfinyl-phenylboronic acid N-methyl-diethanolamine ester (275 mg, 1.0 mmol) was suspended in $CH_2Cl_2$ (2 mL). N-Chlorosuccinimide (147 mg, 1.10 mmol) was added and the mixture was stirred at room temperature for 1 h. Benzylamine (0.23 mL, 2.1 mmol) was added and the reaction mixture was stirred for 1 h at room temperature. Then, Dowex 50WX2-400 cation exchange resin (about 1 g) was added and the mixture was stirred for further 1 h. The resin was removed by filtration and extracted with $CH_2Cl_2$:MeOH (9:1). To the combined organic filtrates was added 1N NaOH and the aqueous phase was washed with $CH_2Cl_2$. The aqueous phase was acidified with 1N HCl and the resulting crystals were isolated by filtration to give 107 mg (37%) of the title compound: $^1$H NMR (DMSO-$d_6$+DCl): δ8.24 (s, 1H), 8.03 (d, 1H), 7.85 (dt, 1H), 7.56 (t, 1H), 7.31–7.21 (m, 5H), 3.96 (s, 2H).

Example 9

3-(Methylphenethylsulfamoyl)benzeneboronic acid

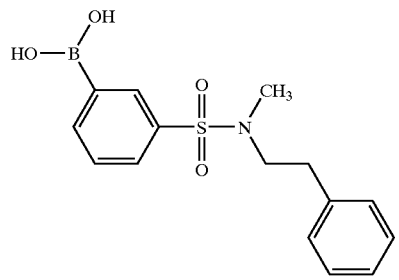

Lithium 3-sulfinyl-phenylboronic acid N-methyl-diethanolamine ester (225 mg, 0.82 mmol) was suspended in $CH_2Cl_2$ (2 mL). N-Chlorosuccinimide (131 mg, 0.98 mmol) was added and the mixture was stirred at room temperature for 1 h. Methylphenylethylamine (0.24 mL, 1.65 mmol) was added and the reaction mixture was stirred for 1 h at room temperature. Then, Dowex 50WX2-400 cation exchange resin (about 1 g) was added and the mixture was stirred for further 1 h. The resin was removed by filtration and extracted with $CH_2Cl_2$:MeOH (9:1). To the combined organic filtrates was added 1N NaOH and the aqueous phase was washed with $CH_2Cl_2$ and then acidified with 1N HCl. The aqueous phase was extracted with $CH_2Cl_2$:MeOH (9:1), dried and then evaporated to give 180 mg (69%) of the title compound as an oil which slowly crystallised: $^1$H NMR (DMSO-$d_6$+DCl): δ8.17 (s, 1H), 8.08 (d, 1H), 7.78 (d, 1H), 7.60 (t, 1H), 7.33–7.19 (m, 5H), 3.18 (t, 2H), 2.77 (t, 2H), 2.69 (s, 3H).

Example 10

3-(Butylmethylsulfamoyl)benzeneboronic acid

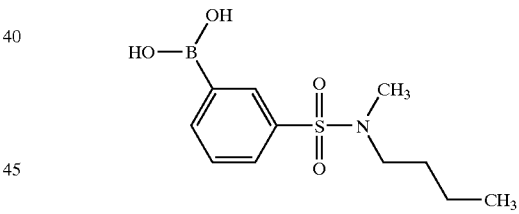

Lithium 3-sulfinyl-phenylboronic acid N-methyl-diethanolamine ester (225 mg, 0.82 mmol) was suspended in $CH_2Cl_2$ (2 mL). N-Chlorosuccinimide (131 mg, 0.98 mmol) was added and the mixture was stirred at room temperature for 1 h. N-Methylbutylamine (0.19 mL, 1.62 mmol) was added and the reaction mixture was stirred for 1 h at room temperature. Then, Dowex 50WX2-400 cation exchange resin (about 1 g) was added and the mixture was stirred for further 1 h. The resin was removed by filtration and extracted with $CH_2Cl_2$:MeOH (9:1). The combined organic filtrates were evaporated, 1N NaOH was added and the aqueous phase was washed with $CH_2Cl_2$ and then acidified with 1N HCl. The aqueous phase was extracted with $CH_2Cl_2$:MeOH (9:1), the extract was dried and then solvent was evaporated to leave 151 mg (68%) of the title compound as an oil which slowly crystallised: $^1$H NMR (DMSO-$d_6$+DCl): δ8.16 (s, 1H), 8.08 (d, 1H), 7.79 (d, 1H), 7.61 (t, 1H), 2.92 (t, 2H), 2.63 (3, 3H), 1.43 (p, 2H), 1.27 (sextet, 2H), 0.87 (t, 3H).

Example 11

3-(Piperidine-1-sulfonyl)benzeneboronic acid

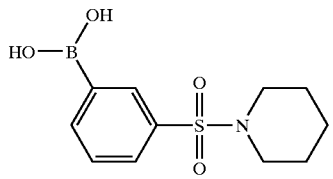

Lithium 3-sulfinyl-phenylboronic acid N-methyl-diethanolamine ester (225 mg, 0.82 mmol) was suspended in $CH_2Cl_2$ (2 mL). N-Chlorosuccinimide (131 mg, 0.98 mmol) was added and the mixture was stirred at room temperature for 1 h. Piperidine (0.17 mL, 1.72 mmol) was added and the reaction mixture was stirred for 1 h at room temperature. Then, Dowex 50WX2-400 cation exchange resin (about 1 g) was added and the mixture was stirred for further 1 h. The resin was removed by filtration and extracted with $CH_2Cl_2$:MeOH (9:1). The combined organic filtrates were evaporated added 1N NaOH and the aqueous phase was washed with $CH_2Cl_2$ and then acidified with 1N HCl. The aqueous phase was extracted with $CH_2Cl_2$:MeOH (9:1), dried and then evaporated to give 167 mg (76%) of the title compound as an oil which slowly crystallised: $^1$H NMR (DMSO-$d_6$+DCl): δ8.12 (s, 1H), 8.10 (d, 1H), 7.72 (d, 1H), 7.63 (t, 1H), 2.86 (t, 4H), 1.57 (p, 4H), 1.35 (bs, 2H).

Example 12

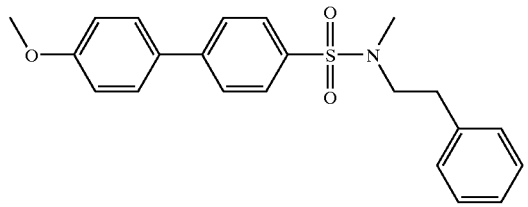

3-(Butylmethylsulfamoyl)benzeneboronic acid (100 mg, 0.313 mmol), KF (60 mg, 1.03 mmol), $Pd_2$(dibenzylidineacetone)$_3$ (9 mg, 0.01 mmol) and Pd(P(t-Bu)$_3$)$_2$ (10 mg, 0.02 mmol) were added to a Schlenk tube under nitrogen. The Schlenk tube was evacuated and refilled with nitrogen five times. Next, 4-bromoanisol (64 mg, 0.34 mmol) in tetrahydrofuran (2 mL) was added. The reaction mixture was stirred at room temperature for 16 h, quenched with aqueous $NH_4Cl$, and extracted with $CH_2Cl_2$, dried and evaporated. Flash chromatography (ethylacetate-heptane 1:4) produced 105 mg (88%) of the title compound as light yellow crystals: mp 97.5° C.; $^1$H NMR (CDCl$_3$): δ7.77 (d, 2H), 7.64 (d, 2H), 7.52 (d, 2H), 7.38 (t, 2H), 7.24–7.17 (m, 3H), 6.98 (d, 2H), 3.84 (s, 3H), 3.28 (t, 2H), 2.87 (t, 2H), 2.78 (s, 3H); $^{13}$C NMR (CDCl$_3$): δ159.95, 144.87, 138.19, 135.44, 131.46, 128.71, 128.49, 128.29, 127.74, 126.92, 126.47, 114.40, 55.27, 51.73, 35.09, 34.74.

Example 13 tert-Butyl 4-amino-N-(4-pinacolboronophenylsulfonyl))butyrate

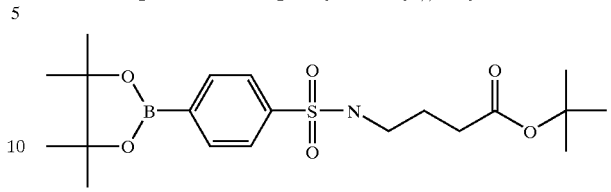

To a suspension of lithium 4-sulfinyl-phenylboronic acid N-methyl-diethanolamine ester (0.55 g, 2 mmol) in dichloromethane (10 ml) N-chlorosuccinimide (0.3 g, 2.2 mmol) was added. The reaction mixture was stirred at room temperature for 1 hour. Then, N,N-diisopropylethylamine (0.23 g, 2.2 mmol) and 4-aminobutyric acid tert-butyl ester hydrochloride (0.43 g, 2.2 mmol) were added. The reaction mixture was stirred at room temperature for another 1 hour. The organic phase was washed with 1 N hydrochloric acid solution followed by water and dried over sodium sulfate. The organic phase was filtered and pinacole (0.26 g, 2.2 mmole) was added. The reaction mixture was stirred at room temperature for 2 hours, and the organic phase was washed twice with water, dried over sodium sulfate and evaporated. The title compound was isolated as oil in 508 mg, 60% yield $^1$H NMR (300 MHz, CDCl$_3$) δ ppm 1.36 (s, 12H) 1.42 (s, 9H) 1.75 (q, J=6.78 Hz, 2H) 2.25 (t, J=6.97 Hz, 2H) 2.99 (q, J=6.66 Hz, 2H) 4.71 (t, J=6.03 Hz, 1H) 7.83 (d, J=8.29 Hz, 2H) 7.93 (d, 2H).

Example 14

Succinimidyl N-(4-pinacolborono-phenylsulfonyl)-4-amino-butyrate

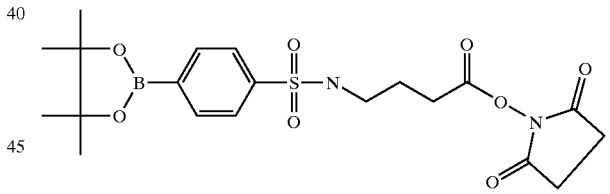

tert-Butyl 4-amino-N-(4-pinacolboronophenylsulfonyl))-butyrate (360 mg, 0.90 mmol) was dissolved in trifluoroacetic acid (8 ml) with cooling to 0° C. The reaction mixture was slowly heated to room temperature and stirred at this temperature for 1 hour. The reaction mixture was evaporated and the crude material was triturated with toluene. The crystalline material was filtered, dried and dissolved in dry dichloromethane. N-hydroxysuccinimide (104 mg, 0.9 mmmol) and N,N'-dicyclohexylcarbodiimide (185 mg, 0.9 mmole) were added and the reaction mixture was stirred at room temperature for 2 hours. The reaction mixture was filtered and evaporated. The crude material was redissolved in ether and filtered to remove N,N'-dicyclohexylurea. The ether solution was evaporated to give the title compound in 470 mg, 87% yield.

$^1$H NMR (300 MHz, CDCl$_3$) δ ppm 1.35 (s, 12H) 1.95 (m, 2H) 2.68 (t, 2H) 2.84 (br. s., 4H) 3.08 (m, 2H) 4.91 (t, 1H) 7.84 (d, J=8.67 Hz, 2H) 7.94 (d, 2H).

Example 15 tert-Butyl N-(4-pinylboronophenylsulfonyl))glycinate

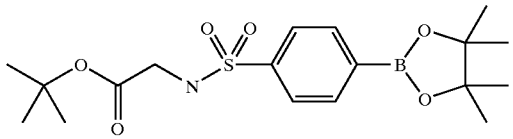

The title compound was prepared by the same procedure as described in Example 13 starting from lithium 4-sulfinyl-phenylboronic acid N-methyl-diethanolamine ester and tert-butyl glycinate hydrochloride. Yield 55%.

$^1$H NMR (300 MHz, CDCl$_3$) δ ppm 1.34 (s, 21H) 3.66 (d, J=5.65 Hz, 2H) 5.02 (t, J=5.28 Hz, 1H) 7.84 (d, J=8.67 Hz, 2H) 7.94 (d, 2H).

Example 16

Succinimidyl N-(4-pinylboronophenylsulfonyl))glycinate

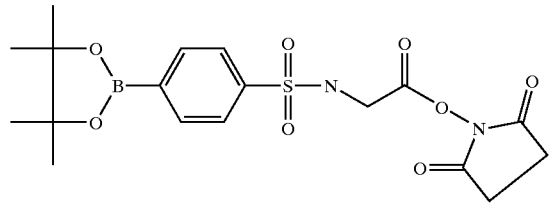

The title compound was prepared by the procedure described in Example 15, starting from tert-butyl N-(4-pinylboronophenylsulfonyl))glycinate. Yield 72%.

$^1$H NMR (300 MHz, CDCl$_3$) δ ppm 1.36 (s, 12H) 2.81 (s, broad, 4H) 4.19 (d, J=6.03 Hz, 2H) 5.18 (t, 1H) 7.85 (d, J=8.29 Hz, 2H) 7.95 (d, 2H).

What is claimed is:

1. A sulfonyl halide of the general formula (I)

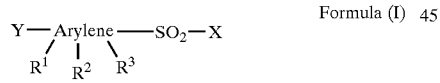

Formula (I)

wherein Arylene designates a carbocyclic or heterocyclic, aromatic ring system comprising 1–3 rings;

R$^1$, R$^2$ and R$^3$ are, independently, hydrogen, C$_{1-6}$alkyl, C$_{1-6}$alkoxy, halogen, nitro, cyano or phenyl;

X is fluoro, chloro or bromo; and

Y is a boroxine moiety attached via a bond from Arylene to one of the boron atoms of a boroxine ring which ring has a group of the formula -Arylene(R$^1$)(R$^2$)(R$^3$)SO$_2$X, wherein Arylene, R$^1$, R$^2$, R$^3$ and X are as defined above, at each of the other two boron atoms of the boroxine ring, or Y is a boronic acid group or a boronic ester group.

2. A compound according to claim 1 wherein Arylene is 1,4-phenylene, 1,3-phenylene or 1,2-phenylene.

3. A compound according to claim 1 wherein R$^1$, R$^2$ and R$^3$ are hydrogen.

4. A compound according to claim 1 wherein X is chloro.

5. A compound according to claim 1 wherein Y is a boronic acid group.

6. A compound according to claim 1 wherein Y is a boronic ester group selected among the options (a)–(g) below wherein the substituent R, when present, is selected from the group consisting of methyl, ethyl, propyl, isopropyl, butyl, isobutyl, tert-butyl and phenyl

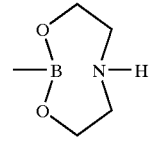
(a)

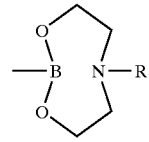
(b)

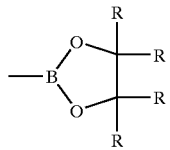
(c)

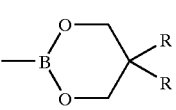
(d)

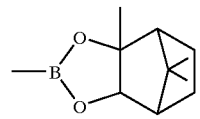
(e)

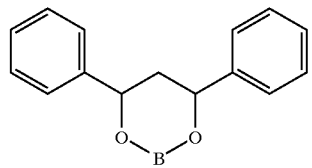
(f)

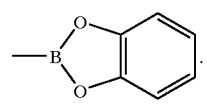
(g)

7. A method of providing a compound of formula (I) according to claim 1 which comprises the following steps:

a) reacting a compound of formula (II):

Formula (II)

wherein R$^1$, R$^2$, R$^3$ and Y are as defined in claim 1, in an inert solvent at a temperature below −75° C. with butyl lithium to form a lithiated intermediate of formula (III):

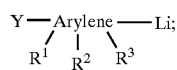

Formula (III)

b) adding sulfur dioxide to the lithiated intermediate of formula (III) to form the corresponding lithium sulfinate of formula (IV):

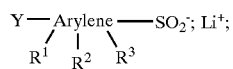

Formula (IV)

and converting the lithium sulfinate of formula (IV) to the corresponding sulfonylchloride of formula (I) by treating the lithium sulfinate with N-chlorosuccinimide or 1,3-dichloro-5,5-dimethylhydantoin or converting the lithium sulfinate of formula (IV) to the corresponding sulfonylbromide of formula (I) by treating the lithium sulfinate with N-bromosuccinimide; or c) adding sulfur trioxide to the lithiated intermediate of formula (III) to form the corresponding lithium sulfonate of formula (V):

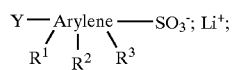

Formula (V)

and converting the lithium sulfonate of formula (V) to the corresponding sulfonylflouride of formula (I) by treating the lithium sulfonate with sulfur tetrafluoride or diethylamino sulfur trifluoride or to the corresponding sulfonylchloride of formula (I) by treating the lithium sulfonate with thionyl chloride, sulfuryl chloride, phosphortrichloride, phosphorpentachloride or phosphoroxychloride.

8. A method according to claim 7 wherein the inert solvent used in step a) is selected from the group of solvents comprising tetrahydrofuran, diethylether, dioxane in mixture with a solvent having a low freezing point, diglyme, tert-butyl-methylether, di-tert-butylether, tetrahydropyran, and mixtures thereof.

9. A method according to claim 7 wherein the temperature at which step a) is carried out is between −75° C. and −150° C.

10. A method according to claim 7 wherein a lithium sulfinate of formula (IV) is converted into the corresponding sulfonylfluoride of formula (I) by treating the lithium sulfinate with sulfur tetrafluoride or diethylamino sulfur trifluoride.

11. A method according to claim 7 wherein a lithium sulfinate of formula (IV) is converted into the corresponding sulfonylchloride of formula (I) by treating the lithium sulfinate with N-chlorosuccinimide or 1,3-dichloro-5,5-dimethylhydantoin.

12. A method according to claim 7 wherein a lithium sulfonate of formula (V) is converted into the corresponding sulfonylchloride of formula (I) by treating the lithium sulfonate of formula (V) with thionyl chloride, sulfuryl chloride, phosphortrichloride, phosphorpentachloride or phosphoroxychloride.

13. A method according to claim 7 wherein a lithium sulfinate of formula (IV) is converted into the corresponding sulfonylbromide of formula (I) by treating the lithium sulfinate with N-bromosuccinimide.

\* \* \* \* \*